(12) United States Patent
Lee

(10) Patent No.: US 10,099,016 B2
(45) Date of Patent: Oct. 16, 2018

(54) SYRINGE PRESSURE GENERATING AND PRESSURE DISPLAYING DEVICE

(76) Inventor: Hee Young Lee, Jeollabuk-do (KR)

(*) Notice: Subject to any disclaimer, the term of this patent is extended or adjusted under 35 U.S.C. 154(b) by 144 days.

(21) Appl. No.: 14/130,628

(22) PCT Filed: Jul. 29, 2011

(86) PCT No.: PCT/KR2011/005621
§ 371 (c)(1),
(2), (4) Date: Mar. 14, 2014

(87) PCT Pub. No.: WO2013/005881
PCT Pub. Date: Jan. 10, 2013

(65) Prior Publication Data
US 2014/0207082 A1    Jul. 24, 2014

(30) Foreign Application Priority Data

Jul. 7, 2011 (KR) ................. 10-2011-0067442

(51) Int. Cl.
*A61M 5/315* (2006.01)
*A61B 5/153* (2006.01)
*A61B 10/02* (2006.01)
*A61M 5/48* (2006.01)
(Continued)

(52) U.S. Cl.
CPC ......... *A61M 5/31581* (2013.01); *A61B 5/153* (2013.01); *A61B 5/150236* (2013.01); *A61B 5/150244* (2013.01); *A61B 10/0283* (2013.01); *A61B 5/15003* (2013.01); *A61B 5/150389* (2013.01); *A61B 5/150503* (2013.01); *A61M 5/3148* (2013.01); *A61M 5/31583* (2013.01);
(Continued)

(58) Field of Classification Search
CPC .......... A61M 5/31581; A61M 5/31578; A61M 5/31586; A61M 5/31583; A61M 5/31545; A61M 5/31548; A61M 3/0216; A61M 5/16854; A61M 5/48; A61M 5/488; A61M 5/28; A61B 5/1405; A61B 5/1545
See application file for complete search history.

(56) References Cited

U.S. PATENT DOCUMENTS 2,653,604 A * 9/1953 Hein, Jr. ................. A61M 5/30
604/68
2,661,740 A * 12/1953 Hickey ................... A61M 5/28
604/193
(Continued)

FOREIGN PATENT DOCUMENTS

EP         0577354 A1    1/1994
EP         1736104 A1    12/2006
WO      WO-97-32156 A1    9/1997

*Primary Examiner* — Bradley J Osinski
*Assistant Examiner* — Nilay Shah
(74) *Attorney, Agent, or Firm* — Polsinelli PC

(57) ABSTRACT

Provided is a syringe pressure generating and pressure displaying device applied to a syringe configured such that an auxiliary device is detachably attached to the cylinder flange while the rod bar is installed in the auxiliary device so as to pass therethrough, and a grip of the hand on a lever that is hinge-connected to the auxiliary device so as to be disposed horizontally in line with the syringe creates a rotational motion due to leverage, whereupon the rotational motion is converted into a linear motion via a motion-converting means, and the rod bar and the piston are moved with increased force.

6 Claims, 11 Drawing Sheets

(51) Int. Cl.
 *A61M 5/31* (2006.01)
 *A61B 5/15* (2006.01)
(52) U.S. Cl.
 CPC ........... *A61M 5/31586* (2013.01); *A61M 5/48* (2013.01); *A61M 5/486* (2013.01)

(56) References Cited

U.S. PATENT DOCUMENTS

| | | | | | |
|---|---|---|---|---|---|
| 4,064,879 | A | * | 12/1977 | Leibinsohn | A61M 5/486 604/121 |
| 4,346,708 | A | * | 8/1982 | LeVeen | A61M 5/486 604/224 |
| 5,961,496 | A | * | 10/1999 | Nielsen | A61M 5/315 604/209 |
| 8,025,657 | B2 | | 9/2011 | Lee | |
| 2010/0105003 | A1 | * | 4/2010 | Weill | A61M 5/3129 433/89 |

* cited by examiner

[Fig. 1]
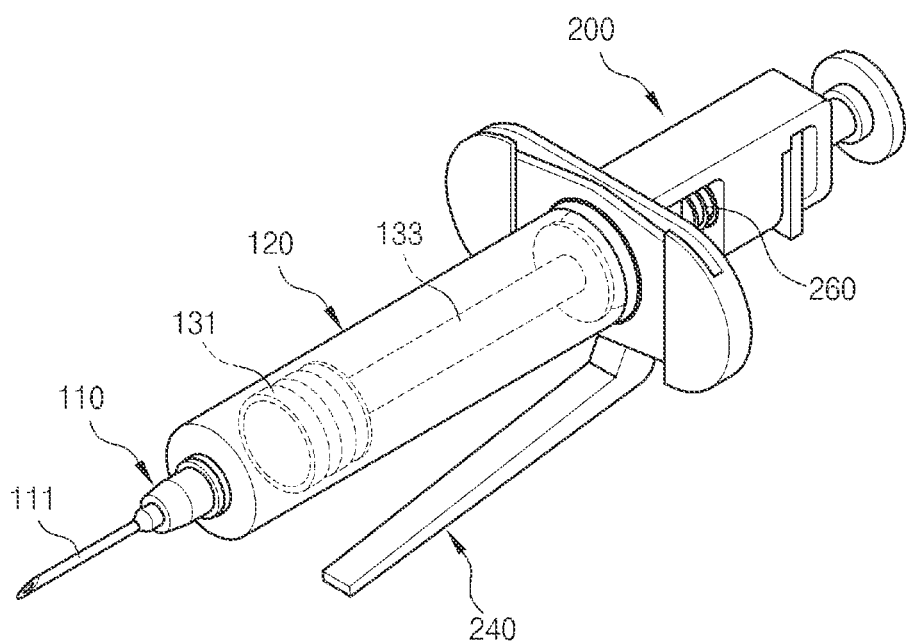

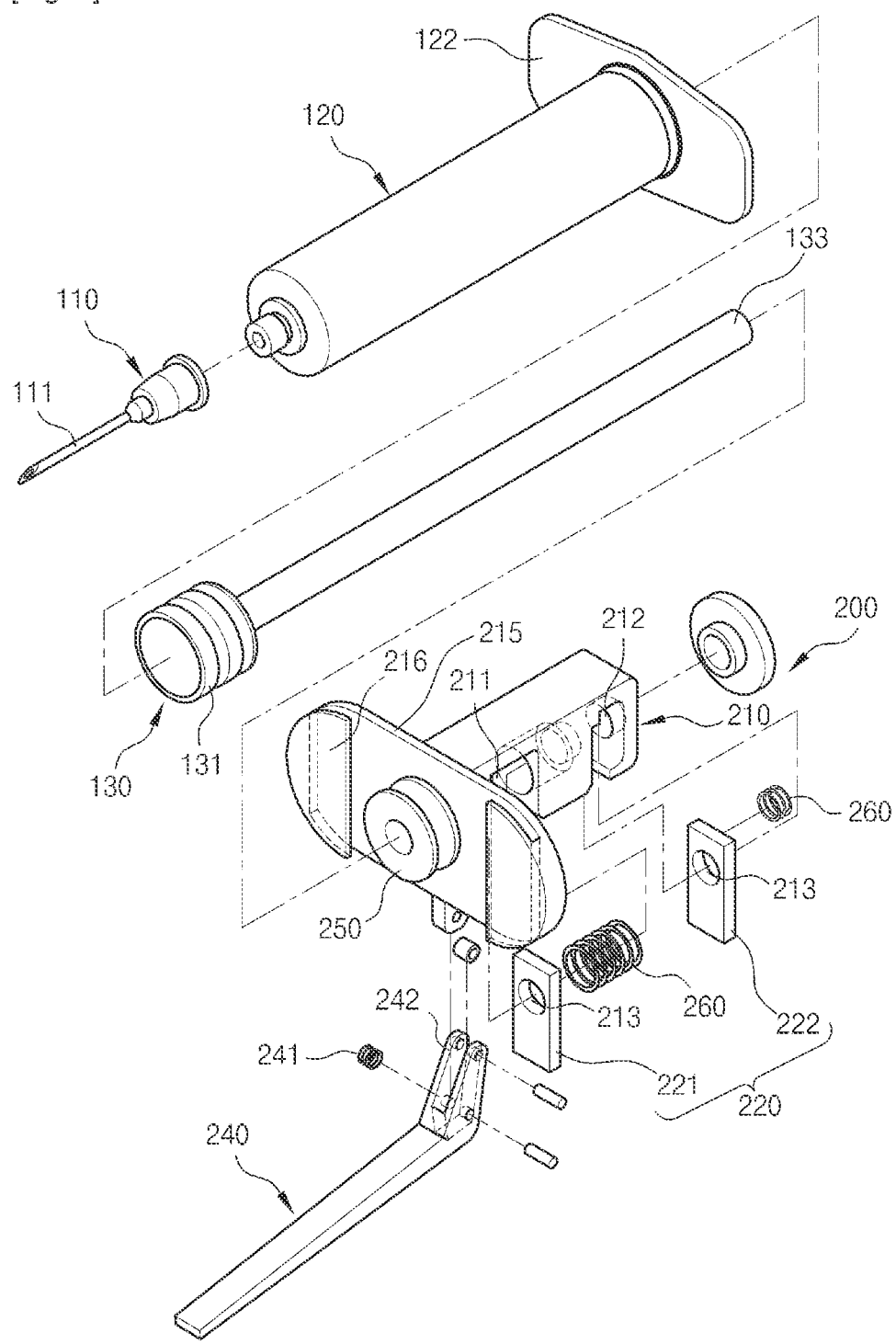
[Fig. 2]

[Fig. 3]
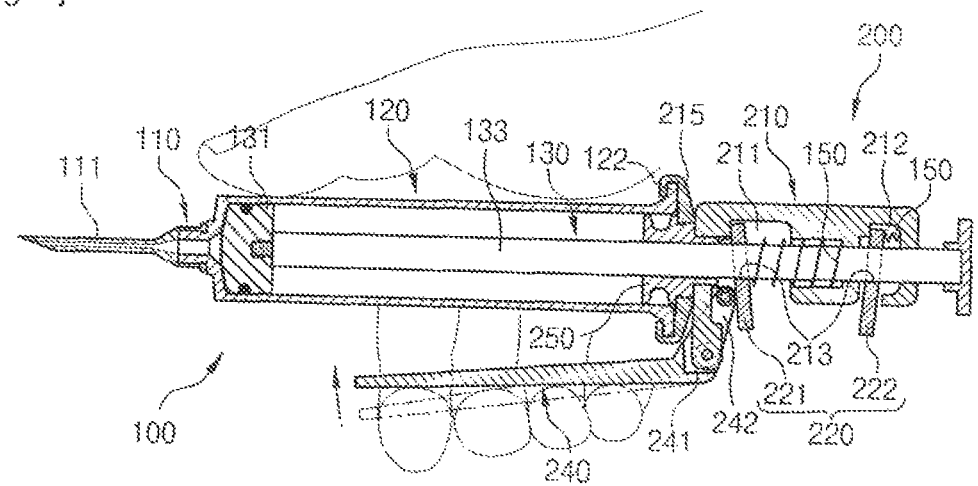
[Fig. 4]
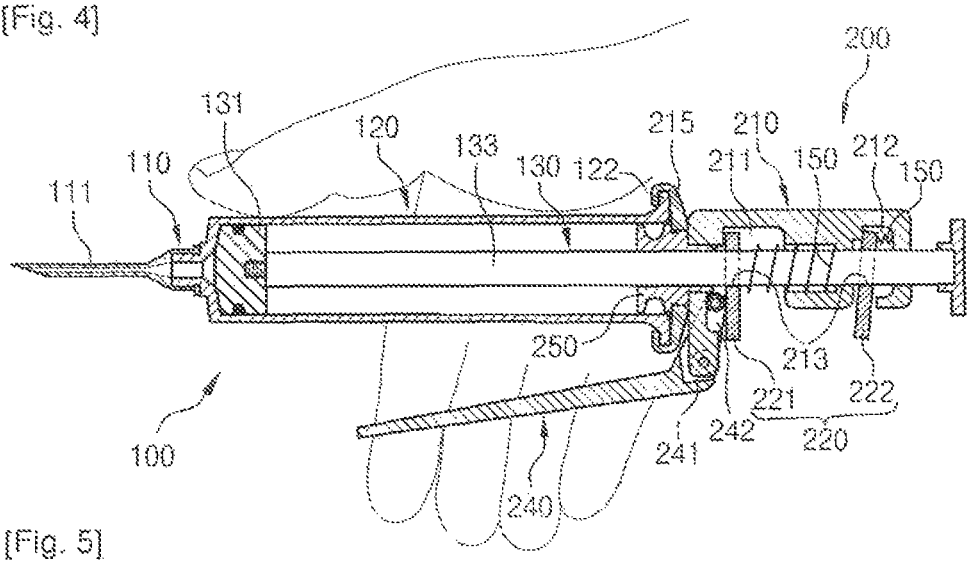
[Fig. 5]
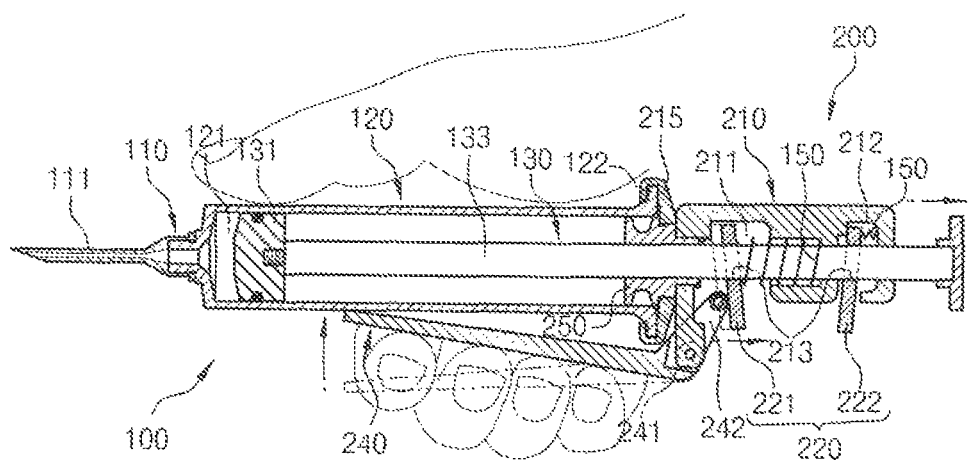

[Fig. 6]
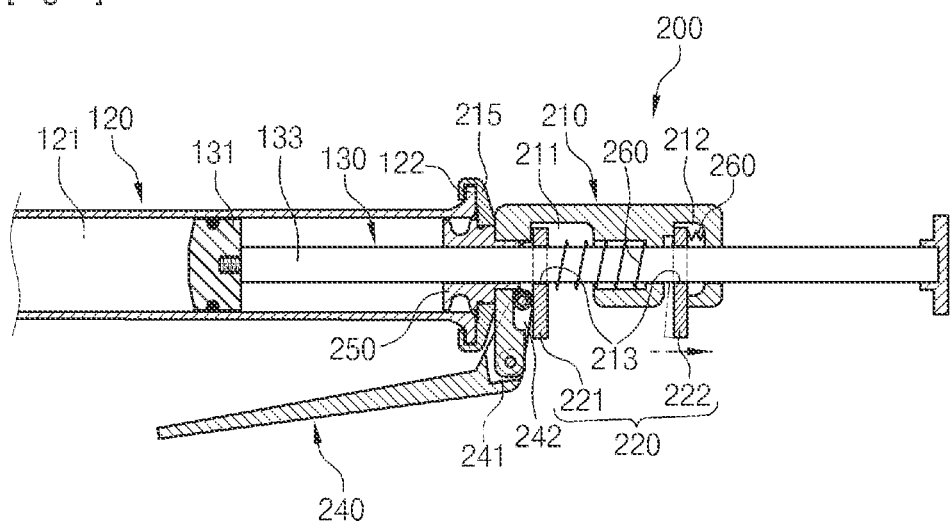
[Fig. 7]
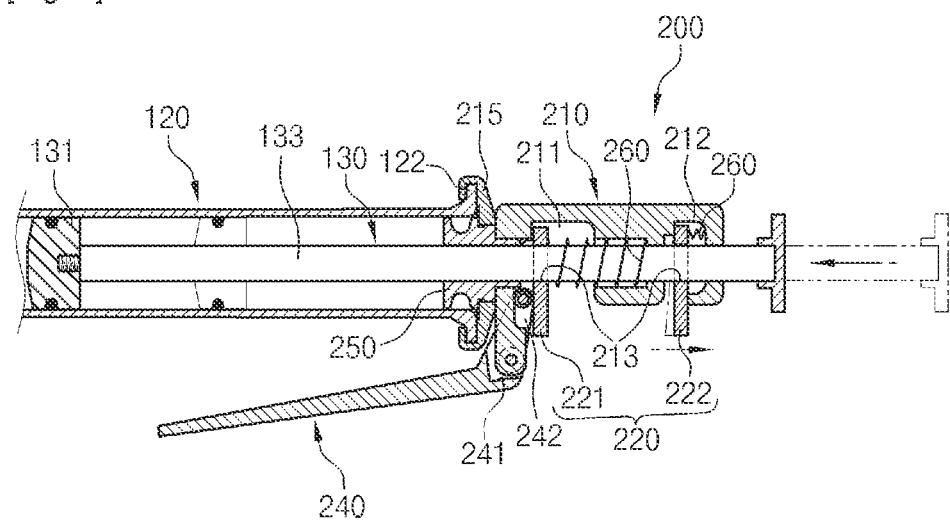

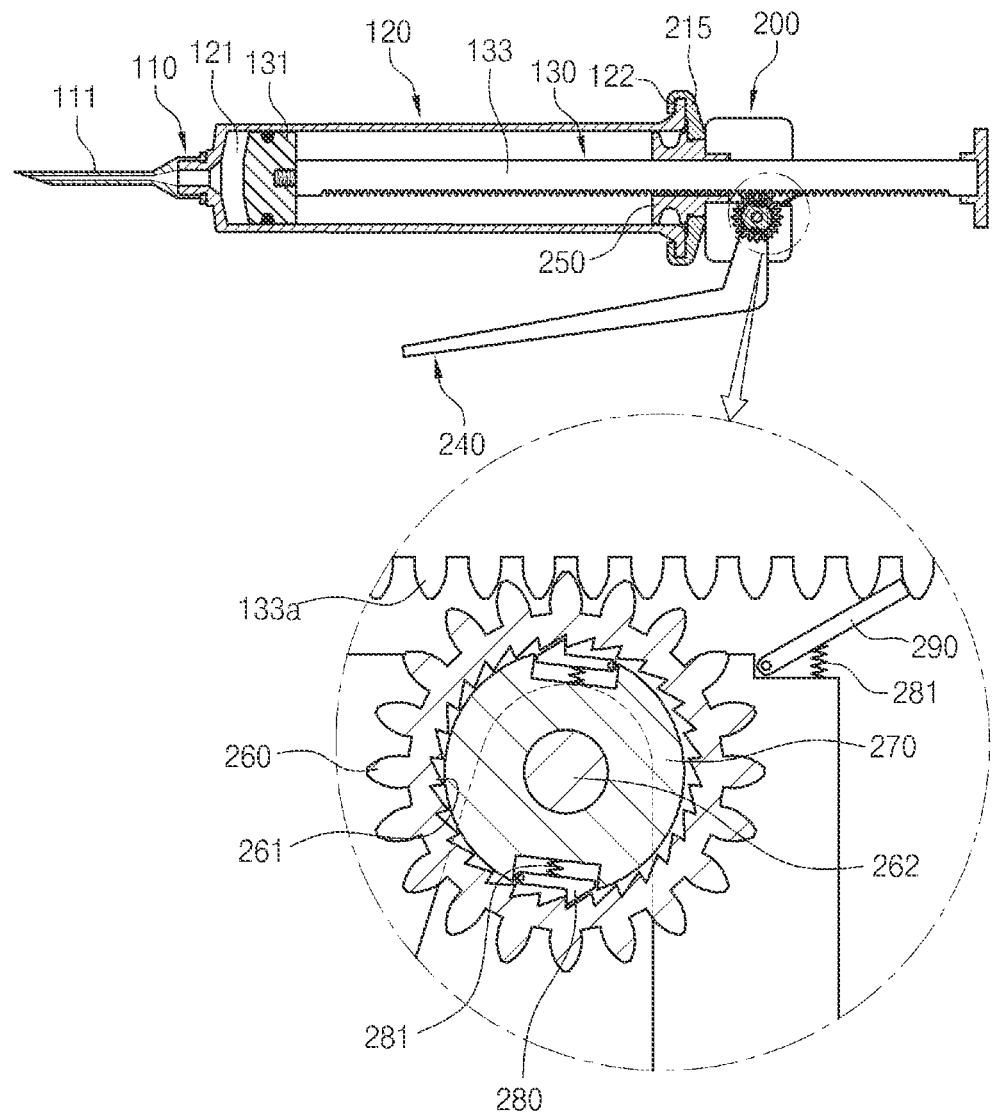
[Fig. 8]

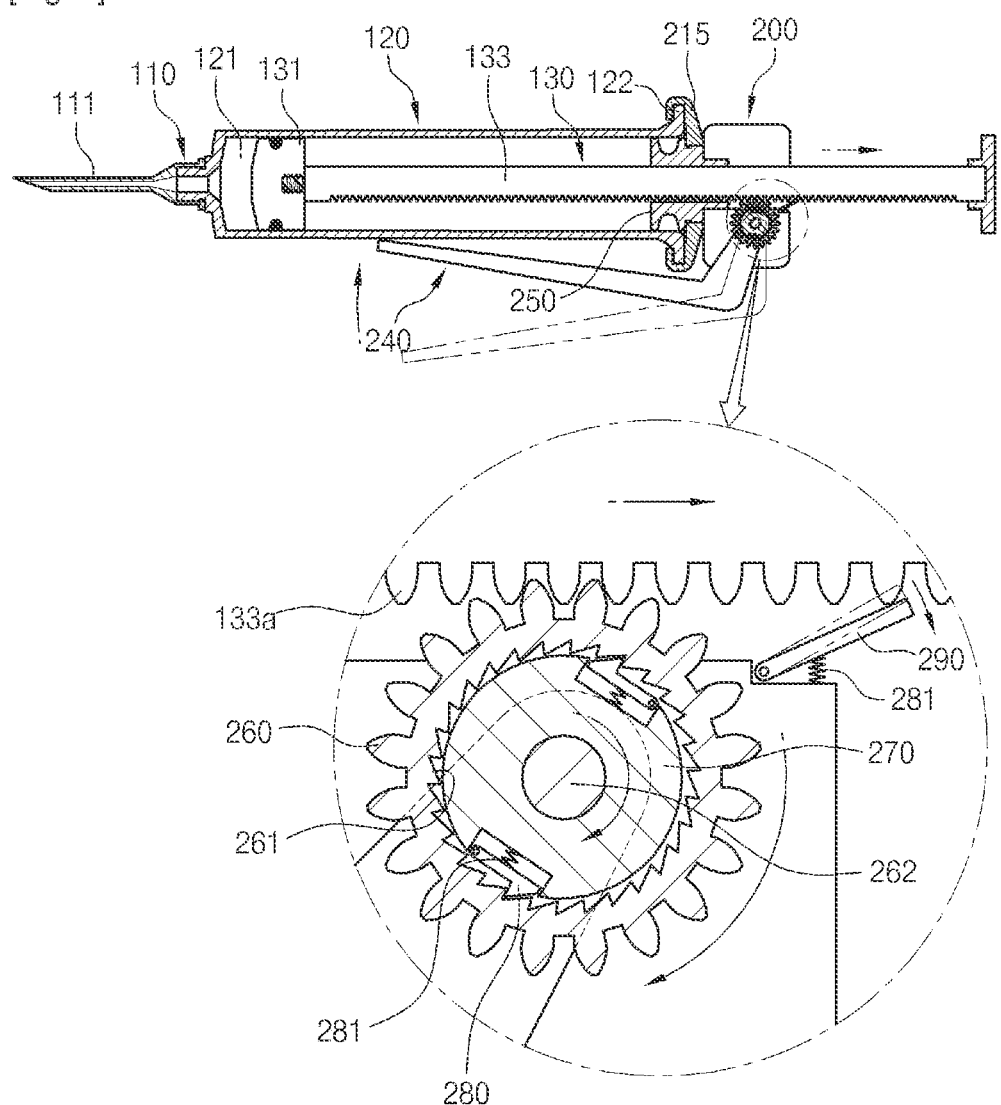
[Fig. 9]

[Fig. 10]
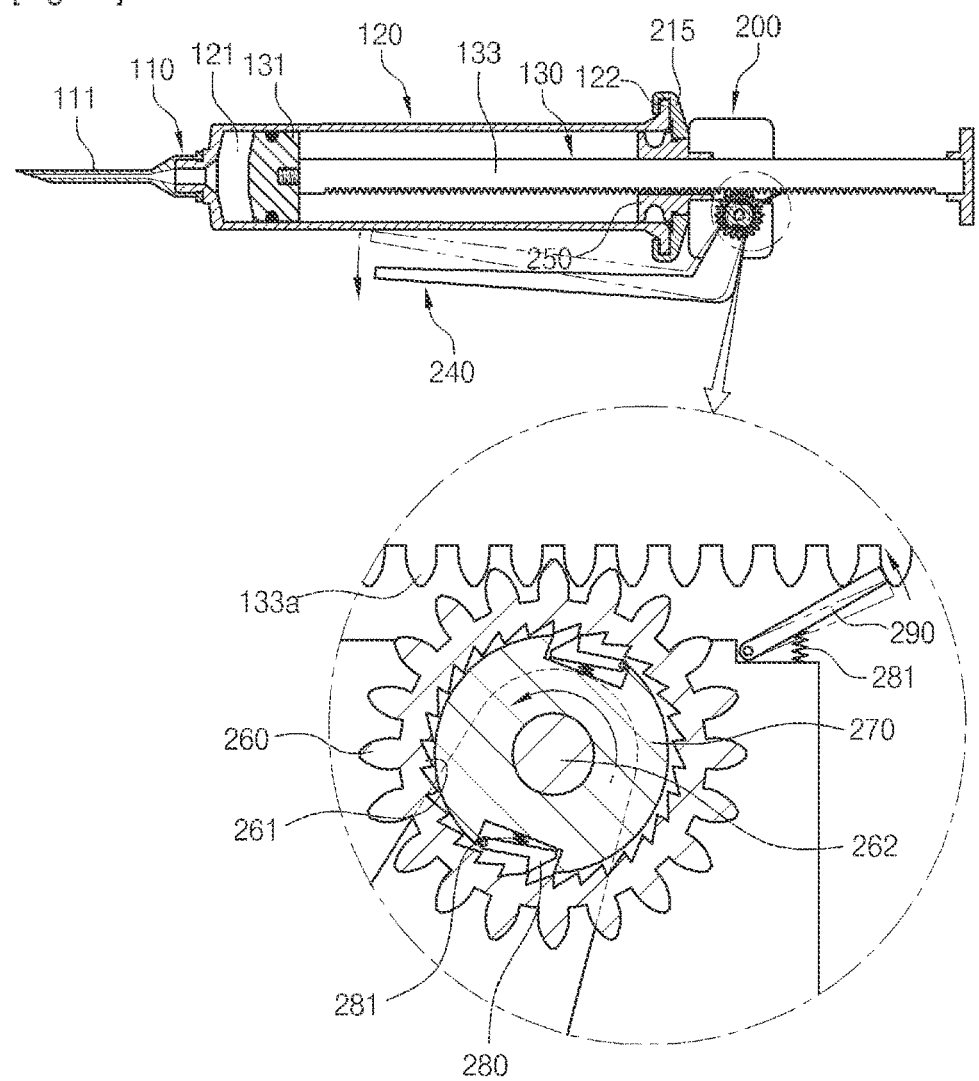
[Fig. 11]
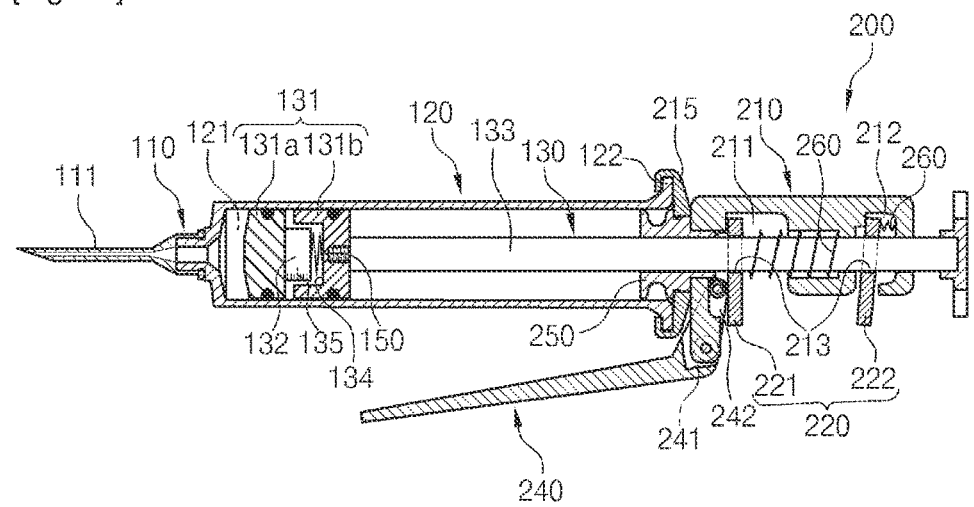

[Fig. 12]
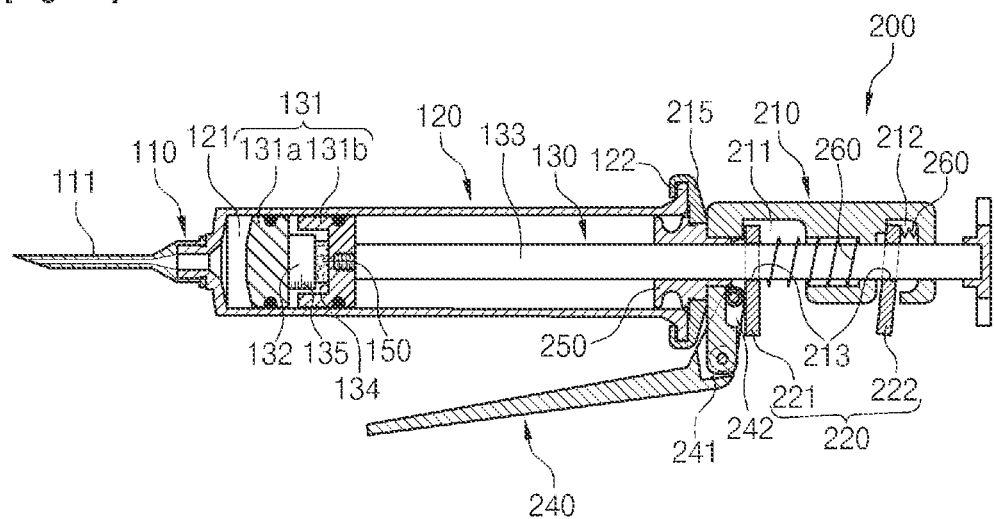
[Fig. 13]
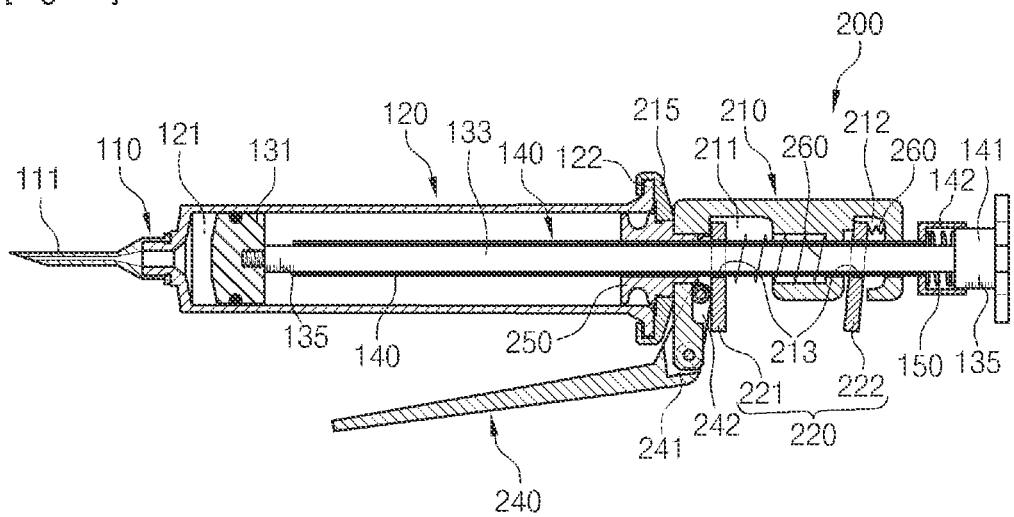

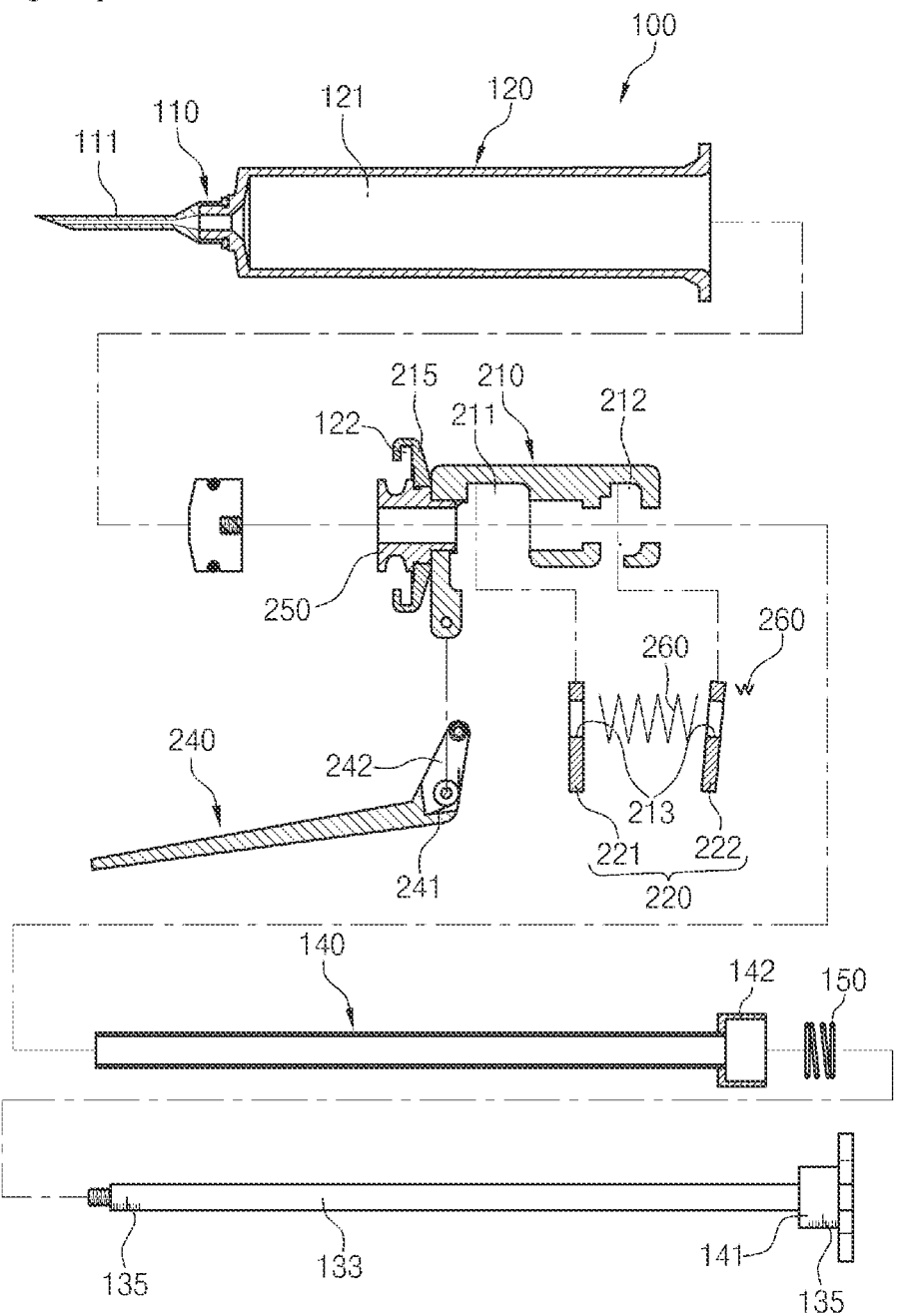
[Fig. 14]

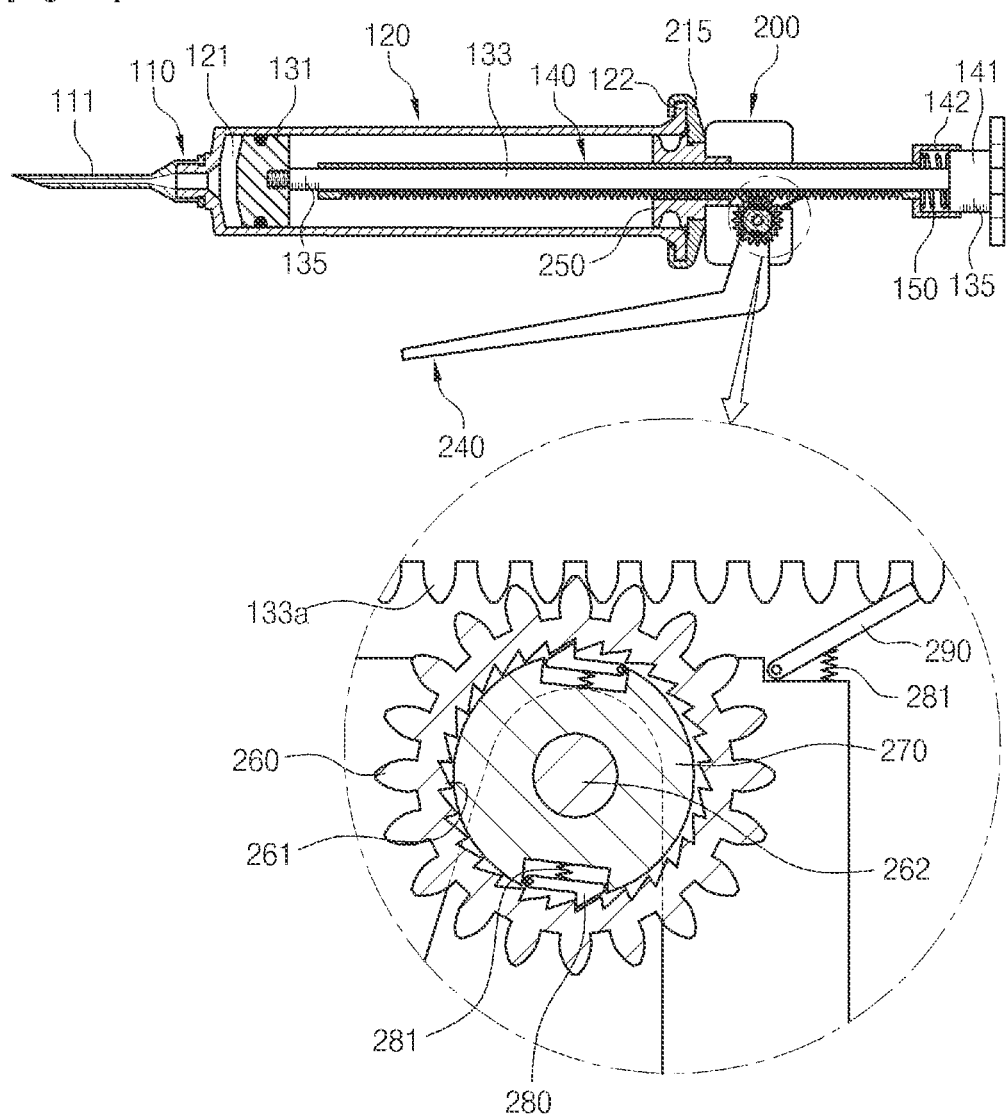
[Fig. 15]

[Fig. 16]
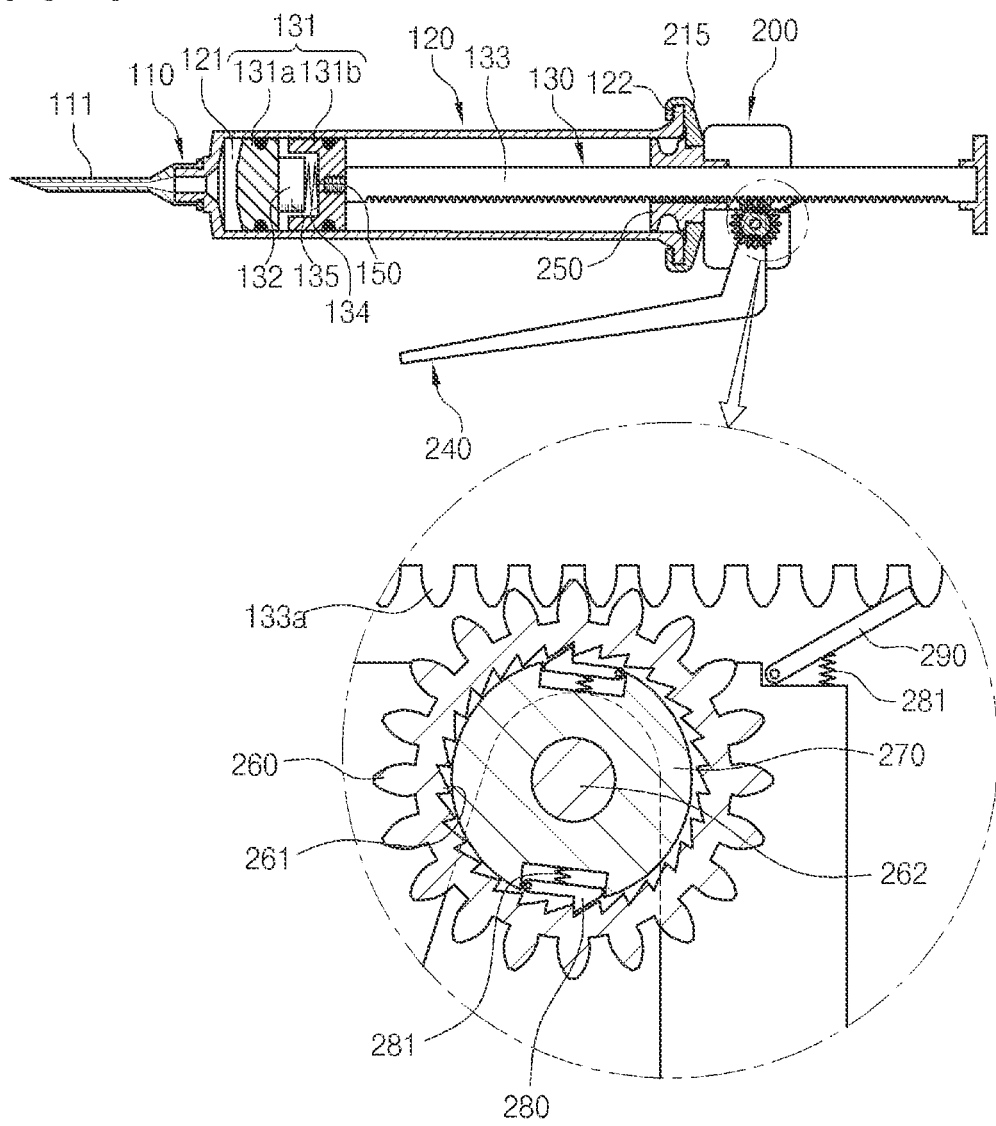

SYRINGE PRESSURE GENERATING AND PRESSURE DISPLAYING DEVICE

CROSS REFERENCE TO RELATED APPLICATIONS

This application is a National Phase filing under 35 U.S.C. § 371 of PCT/KR2011/005621 filed on Jul. 29, 2011; and this application claims priority to Application No. 10-2011-0067442 filed in Republic of Korea on Jul. 7, 2011; the entire contents of all are hereby incorporated by reference.

TECHNICAL FIELD

The present invention relates, in general, to a syringe pressure generating and pressure displaying device and, more particularly, to a syringe pressure generating and pressure displaying device that enables an injection procedure for injecting fat or medicine to be easily performed by generating pressure using a grip of one hand and also enables the intensity of syringe pressure to be easily confirmed.

BACKGROUND ART

Generally, a syringe is a tool used to inject a medicinal fluid into human tissue and is composed of: a tip portion to which a needle is connected; a cylinder insertedly connected to the tip portion and having a space; and a rod bar connected to the space and for injecting medicine or extracting human tissue through a needle using a positive pressure or a negative pressure generated by increasing pressure of the space by being linked with a pulling or pushing motion of the rod bar.

Here, a flange is formed to protrude at an end of the cylinder and an end of the rod bar, respectively.

When medicine is injected into the human body or human tissue is extracted through the syringe configured as above, negative pressure is generated by a motion of sticking a needle into the body, and then pulling the rod bar backward in a state of holding onto the cylinder and the rod bar using both hands, thereby extracting the human tissue, or the positive pressure is generated by a motion of pushing the rod forward, thereby injecting medicine into the body.

However, when injecting medicine or extracting human tissue using the syringe according to the conventional art, an operator's one hand is used to help enable easy injection or extraction such as rubbing an injection site and to correct an injection subject's posture, and another hand is used to move the rod bar of the syringe forward or backward.

At this time, an injecting motion of the syringe using one hand is performed by grasping the cylinder and the flange of the rod bar with the fingers and moving them forward or backward in such a state. However, it is problematic in that the injecting motion may cause a mistake of the injection procedure by increasing inconvenience.

Also, when injecting a lot of medicine into the body using a high-capacity syringe or injecting viscous medicine, in a case where a high positive pressure is generated in a space inside the syringe, it is problematic in that the tip portion insertedly connected to the cylinder is separated.

In reverse, during extracting viscous fat from the human body during a transplantation procedure of fat for correcting a shape of the body, when a high negative pressure is generated in the space inside the syringe, it is problematic in that it is difficult to perform the pulling motion of the rod bar using one hand.

Moreover, when performing a liposuction operation, fat is sucked inside the syringe space through the needle in such a manner as to put the needle into the body, and then pull out the rod bar mounted with a piston backward to generate a negative pressure inside the syringe. At this time, when a tip of the needle is exposed to the air due to the operator's mistake, the negative pressure inside the syringe is destroyed, whereupon liposuction is discontinued.

In reverse, in the procedure of injecting medicine into the body, the operator should inject the medicine by generating a positive pressure by applying constant power according to different kinds of viscosity of each medicine, but when positive pressure is excessively generated, it is problematic that tissue around an injection site of the body may be damaged.

As a result, since the generation of a stable positive or negative pressure of the syringe depends completely on the operator's judgment based on physical resistance felt from his or her hand, it is problematic in that it is difficult to accurately perform a fat extraction procedure or a medicine injection procedure.

DISCLOSURE

Technical Problem

Accordingly, the present invention has been made keeping in mind the above problems occurring in the prior art, and an object of the present invention is to provide a syringe pressure generating and pressure displaying device which enables human tissue to be easily extracted through a syringe to the outside using a grip of one hand.

Another object of the present invention is to provide a syringe pressure generating and pressure displaying device which can continuously generate a negative pressure while keeping a pressure situation even during the generation of the negative pressure.

A further object of the present invention is to provide a syringe pressure generating and pressure displaying device which enables a negative pressure to be released by a simple mechanical operation.

Yet another object of the present invention is to provide a syringe pressure generating and pressure displaying device which can selectively generate a negative pressure or a positive pressure inside a syringe.

Still another object of the present invention is to provide a syringe pressure generating and pressure displaying device which enables an operator to confirm the pressure situation of an internal space in a syringe with the naked eye when injecting fat and medicine or extracting a human tissue using the syringe.

Still further another object of the present invention is to provide a syringe pressure generating and pressure displaying device which enables an operator to confirm the variable pressure situation of a negative pressure or a positive pressure in the internal space of a syringe using gradations, thereby enabling the operator to operate on injection while checking a more accurate change.

Still yet another object of the present invention is to provide a syringe pressure generating and pressure displaying device which is intended to prevent the overload of pressure by generating the pressure in an indirect transfer method for supplementing the disadvantage of an existing hand syringe or simple pressure syringe which may generate the overload of pressure.

Technical Solution

In order to accomplish the above object(s), the present invention provides a syringe pressure generating and pressure displaying device, which is applied to a syringe including: a tip portion to which a needle is connected; a cylinder connected to the tip portion to form a space therein, and having cylinder flange formed in an opening end of the space; a pressure means configured to inject medicine or extract a human tissue through the needle using a negative pressure or a positive pressure generated by changing pressure of the space with a piston being linked with a pushing or pulling motion of rod bar connected to the piston in the space using the fingers, wherein an auxiliary device is detachably attached to the cylinder flange while the rod bar is installed in the auxiliary device so as to pass therethrough, and a grip of the hand on a lever that is hinge-connected to the auxiliary device so as to be disposed horizontally in line with the syringe creates a rotational motion acting due to leverage, whereupon the rotational motion is converted into a linear motion via a motion-converting means, and the rod bar and the piston are moved with increased force.

According to the present invention, the auxiliary device may be configured such that a main block fixed to the cylinder flange so as to disposed horizontally in line with the cylinder is provided, and a movable block and a fixed block each provided with a through hole for enabling the rod bar to pass through by forming a movable space and a fixed space each having an open lower part are disposed in the main block, wherein a negative pressure may be generated in such a manner that the movable block and the fixed block are in close contact with the movable space and the fixed space in one direction by an elastic member, respectively, and thus by rotation of the lever which is hinge-connected to the front of the main block, a lower part of the movable block is pushed by a pressing projection formed at an end of the lever so as to cause an inclination change and so as to be moved backward, whereupon an outer circumferential surface of the rod bar is pressed by upper and lower corners of an internal circumference of the through hole in a lower direction, thereby enabling the rod to be moved to the rear of the cylinder, and at the same time, the lever is recovered in its original state through a spring mounted to a hinge-connected part when a grip is released, and the movable block is maintained in an erect situation with the rod bar by the elastic member so as to arrange forward movement in next order.

According to the present invention, a guide block through which the rod bar passes may be connected to an inlet of the space of the cylinder so as to support movement of the rod bar.

According to the present invention, a fixing clip having a fixing jaw formed at the front thereof may be installed in the main block so that the cylinder flange can be detachably inserted into the fixing jaw by rotation of the cylinder flange.

According to the present invention, the fixed block may be installed in the fixed space so that a lower part of the fixed block can be partially exposed, and so as to pass through the rod bar, and may be installed to be inclined by the elastic member so that the outer circumferential surface of the rod bar can be pressed by upper and lower parts of the internal circumference of the through hole in a lower direction, thereby enabling the rod bar moved by the movable block to be immovably fixed thanks to the negative pressure, wherein when a fixing situation of the rod bar is released, by pulling out the lower part of the fixed block and converting the fixed block into an erect situation with the rod bar, the through hole of the rod bar enables the outer circumferential surface of the rod bar to be released from a pressure situation.

According to the present invention, the motion-converting means may be synchronized with a rack gear formed at one end of the rod bar in a length direction by rotatably installing a pinion gear through a central axis in the auxiliary device, an internal gear having an inclination angle only in one direction may be installed inside the pinion gear, and a latch gear elastically synchronized with the internal gear through the spring may be installed in a rotating sphere connected to the lever, so the lever enables the pinion gear to transmit rotational force to the internal gear only in one direction.

According to the present invention, an auxiliary latch gear may be hinge-connected to the rear of the auxiliary device, and then one end thereof may be elastically located upward by the spring so that the movement of the rod bar can be controlled by the negative pressure generated at the syringe.

According to the present invention, the grip may go through the elastic member during transmitting the grip to the piston so that a change amount in a tensioned shape of the elastic member can be changed by the intensity of transmitted pressure, thereby enabling the operator to confirm the intensity of pressure to the outside through measurement of the change amount in the shape of the elastic member.

According to the present invention, the elastic member connected to the rod bar may be pressed during transmitting the grip to the piston so that a change amount in a pressed shape of the elastic member can be changed by the intensity of transmitted pressure, thereby enabling the operator to confirm the intensity of pressure to the outside through measurement of the change amount in the shape of the elastic member.

According to the present invention, the piston may be configured such that a first piston and a second piston formed in a double structure are connected to the space of the cylinder, and a confirmation member is formed at one side of the first piston, a groove for receiving the confirmation member is formed in the second piston so that a negative or positive pressure can be selectively generated in the space of the cylinder by connecting the confirmation member of the first piston and the groove of the second piston using the elastic member and moving the first piston using the elastic member being linked with the second piston via the rod bar, wherein intensity of the negative or positive pressure generated in the space can be confirmed based on a changed shape length of the elastic member due to its own elasticity through gradations of each unit displayed on an external circumference of the confirmation member.

According to the present invention, a housing slidably connected on an outer circumference of the rod bar may be provided such that a cover is fixed to one end of the housing, and a button is fixed to one end of the rod bar so that the button is partially received inside the cover, wherein a negative pressure is generated in such a manner that when the elastic member is fixed inside the cover, and the housing is moved by the lever, the elastic member is pressed, and thus when compressive force of the elastic member is equal to or higher than pressure of the space of the cylinder, the button is indirectly moved backward, thereby interlocking the rod bar, wherein gradations of each unit are displayed on the button and the external circumference of the rod bar so as to enable the operator to confirm a changed shape length of the elastic member due to the self-elasticity of the elastic member and thus to check intensity of the negative pressure or positive pressure.

According to the present invention, the elastic member may be composed of rubber or a spring.

Advantageous Effects

A syringe pressure generating and pressure displaying device according to an embodiment of the present invention is effective in enabling human tissue to be easily extracted through a syringe by only a grip of one hand because a rod bar can be gradationally moved in one direction via a movable block being extendably mounted to a cylinder and being linked with a lever which is rotated by the grip of one hand.

Also, the syringe pressure generating and pressure displaying device according to the embodiment of the present invention is effective in improving efficiency for the extraction of human tissue because the rod bar can be prevented from being moved in an opposite direction using a negative pressure through a fixed block installed at a main block being extendably mounted to the cylinder when the rod bar is gradationally moved by being linked with rotation of the lever according to a repeated motion for the grip of one hand, thereby enabling negative pressure to be continuously generated in a constant pressure situation even during generation of the negative pressure.

Moreover, the syringe pressure generating and pressure displaying device according to the embodiment of the present invention is effective in improving an operational property of a pressure generating auxiliary device and in selectively generating the negative pressure and the positive pressure because a fixing situation can be released by changing an inclination of the fixed block mounted to the main block and functioning to maintain the negative pressure state, so the negative pressure situation of a space of the cylinder can be simply released by simple motion conversion of the fixed block.

Also, the syringe pressure generating and pressure displaying device according to the embodiment of the present invention is effective in minimizing a mistake of an injection procedure from preventing the overload of pressure by generating pressure in an indirect transfer method of power through the elastic member thanks to the following configurations:

In order to supplement a disadvantage that an existing hand syringe or simple pressure syringe may cause an overload of pressure, a first piston and a second piston are closely connected to an inner wall of the space, and the elastic member is connected between the first piston and the second piston, so the second piston is moved by the rod bar connected to the second piston and extending to the outside of the space of the cylinder and is then linked with the first piston by pressure of the elastic space, thereby enabling a positive pressure or negative pressure to be generated in the space.

In addition to, a housing is slidably connected to an end of the rod bar exposed to the outside of the cylinder, and then the button and cover fixed to the end of the rod bar and an end of the housing are connected, and at the same time, the elastic member is entered inside the cover, so movement of the housing by the lever is transferred to the cover, the elastic member, and then button in order, thereby being linked with the piston by the rod bar fixed to the button to enable a negative pressure or positive pressure to be generated.

Furthermore, the syringe pressure generating and pressure displaying device according to the embodiment of the present invention is effective in enabling an accurate injection procedure for injecting fat or medicine or extracting human tissue to be performed because gradations of each unit are displayed on a confirmation member installed at the first piston when a negative or positive pressure is generated at the syringe so that a shape change situation due to self-elasticity of the elastic member can be confirmed with the naked eye, and at the same time, a pressure change can be confirmed using the gradations of each unit, thereby enabling the operator to accurately check the intensity of pressure generated in the syringe space.

Also, the syringe pressure generating and pressure displaying device according to the embodiment of the present invention is effective in improving the visibility of pressure because gradations of each unit are displayed on the rod bar and the button in the pressure displaying device composed of the rod bar, the housing, the cover and the button so that a change state of pressure intensity can be more easily be checked.

DESCRIPTION OF DRAWINGS

FIG. 1 is a perspective view showing a state in which an auxiliary device according to one embodiment of the present invention is mounted to a cylinder;

FIG. 2 is an exploded perspective view showing a state in which the auxiliary device according to the one embodiment of the present invention is mounted to the cylinder;

FIGS. 3 to 7 are cross-sectional views showing phased operating states of the auxiliary device according to the one embodiment of the present invention;

FIG. 8 to FIG. 10 are views showing an operation order of a motion-converting means according to another embodiment of the present invention;

FIGS. 11 and 12 are cross-sectional views showing a state in which a displaying device according to one embodiment is mounted to a syringe pressure generating device of the present invention; and FIG. 13 to FIG. 16 are cross-section views showing a state in which a display device according to another embodiment is mounted to the syringe pressure generating device of the present invention.

| <Description of the Reference Numerals in the Drawings> | |
|---|---|
| 100: Syringe | 110: Tip portion |
| 111: Needle | 120: Cylinder |
| 121: Space | 122: Cylinder flange |
| 130: Pressure means | 131: Piston |
| 131a: First piston | 131b: Second piston |
| 132: Confirmation member | 133: Rod bar |
| 133a: Rack gear | 134: Groove |
| 135: Gradations | 140: Housing |
| 141: Button | 142: Cover |
| 150: Elastic member | 200: Auxiliary device |
| 210: Block | 211: Movable space |
| 212: Fixed space | 213: Through hole |
| 215: Fixing clip | 216: Fixing jaw |
| 220: Motion-converting means | |
| 221: Movable block | |
| 222: Fixed block | 240: Lever |
| 241: Spring | 242: Pressing projection |
| 250: Guide block | 260: Pinion gear |
| 261: Internal gear | 262: Central axis |
| 270: Rotating sphere | 280: Latch gear |
| 281: Spring | 290: Auxiliary latch gear |
| 300: Displaying device | |

BEST MODE

Hereinbelow, embodiments of the present invention will be described in detail with reference to the accompanying drawings.

Reference should now be made to the drawings, in which the same reference numerals are used throughout the different drawings to designate the same or similar components. In the following description, it is to be noted that, when the functions of conventional elements and the detailed description of elements related with the present invention may make the gist of the present invention unclear, a detailed description of those elements will be omitted.

FIG. 1 is a perspective view showing a state in which an auxiliary device of the present invention is mounted to a cylinder, FIG. 2 is an exploded perspective view showing a state in which the auxiliary device of the present invention is mounted to the cylinder, FIGS. 3 to 7 are cross-sectional views showing phased operating states of the auxiliary device of the present invention, FIGS. 8 to 10 are views showing an operation order of a motion-converting means according to a different embodiment of the present invention, FIGS. 11 and 12 are cross-sectional views showing a state in which a displaying device according to one embodiment is mounted to a syringe pressure generating device of the present invention, and FIGS. 13 to 16 are cross-section views showing a state in which a display device according to another embodiment is mounted to the syringe pressure generating device of the present invention.

First, as illustrated in FIG. 1 to FIG. 7, a syringe to which a syringe pressure generating and displaying device according to the present invention is applied is configured as follows.

A syringe 100 includes: a tip portion 110 to which a needle 111 is connected; a cylinder 120 connected to the tip portion 110, and having a space 121 therein and a cylinder flange formed at an opening end of the space 121; and a pressing means 130 for injecting medicine or extracting human tissue through the needle using a positive pressure or a negative pressure generated by changing pressure of the space 121 with a piston 131 linked by pushing or pulling the rod bar 133 linked with the piston 131 connected to the space with the fingers.

The tip portion 110 may be connected to and separated from the cylinder 120, and a protruding jaw (no reference numeral) is formed at an opposite end part of the tip portion 110 to which the needle 111 is mounted.

Furthermore, the cylinder 120 has a cylindrical shape, and the pressing means 130 composed of the piston 131 linked with the rod bar 133 is connected to the space 121 of the cylinder 120, thereby enabling a positive pressure or a negative pressure to be generated in the space 121 along a movement direction of the piston 131.

Negative pressure is generated in the space 121 by pulling the piston 131 to the rear of the cylinder 120 through the rod bar 133, and is used when extracting human liquid tissue to the space 121 through the needle 111 penetrated into the human body.

In reverse, the positive pressure is generated by pushing the piston 131 to the front of the cylinder 120 through the rod bar 133 and is used when injecting a liquid drug filled in the space 121 into the human body through the needle 111 penetrated into the human body.

A pressure generating auxiliary device 200 in the syringe 100 configured as above is detachably attached to the cylinder flange 122 while the rod bar 133 is installed in the auxiliary device 200 so as to pass therethrough, and a grip of the hand on a lever 240 that is hinge-connected to the auxiliary device 200 so as to be disposed horizontally in line with the syringe creates a rotational motion acting due to leverage, whereupon the rotational motion is converted into a linear motion via a motion-converting means 220, and the rod bar 133 and the piston 131 are moved with increased force at low speed.

The auxiliary device 200 is provided with a main block 210 to which the rod bar 133 is connected to pass through, and which is fixed to a cylinder flange 122.

In the front of the main block 210, a fixing clip in which a fixing jaw 216 is formed is inserted into the cylinder flange 122 by rotation, whereupon the main block 210 is fixed to the cylinder flange 122 of the cylinder 120 to extend horizontal thereto, and the rod bar 133 exposed to the cylinder 120 passes through the main block 210.

Here, the rod bar 133 is screw-connected to the piston, and a guide block 250 through which the rod bar 133 passes is connected to an inlet of the space 121 of the cylinder 120 while the guide block 250 is fixed to the main block 210 by passing through the fixing clip 215 so that the guide block 250 can support movement of the rod bar 133.

The main block 210 connected to the cylinder 120 is configured as follows.

The motion-converting means 220 is installed in the main block 210.

The motion-converting means 220 is formed so that an movable space 211 and a fixed space 212 each having an opening at a lower part thereof are divided, thereby installing an movable block 221 and a fixed block 222 in the movable space and the fixed space, respectively.

Here, a through hole 213 is formed in the movable block 221 and the fixed block 222, respectively, so that the rod bar can pass therethrough.

As such, in the main block, the movable block 221 and the fixed block 222 are installed to be spaced apart from each other while the rod bar 133 passes therethrough, and then the movable block 221 and the fixed block 222 come into close contact with the main block 210 in one direction by an elastic member 260.

Furthermore, the lever 240 that is horizontally and separately hinge-connected to the cylinder 120 and has a spring 241 formed therein is mounted to a lower part of the front of the main block 210, and a pressing projection 242 bent to one side of the lever 240 is located at a lower part of the front of the movable block 221.

Here, depending on a perpendicular or inclination direction of the movable block 221 and the fixed block 221, a movement or fixation state of the rod bar 133 is determined.

That is, the initial movable block 221 is maintained in an erect state with the rod bar 133, and the fixed block 222 is disposed in a state that an upper part thereof has a slope inclined in an end direction of the rod bar 133.

After this, when the lower part of the movable block 221 is pushed by the pressing projection 242 by rotation of the lever 240, the slope is changed, whereupon an outer circumferential surface of the rod bar 133 is pressed by upper and lower corners of an inter circumference of the through hole 213 in a lower direction so that the rod bar can be moved to the rear of the cylinder 120, thereby enabling a negative pressure to be generated in the space 121 of the cylinder.

Next, when a grip is released from the lever 240, the lever 240 is recovered to its original state, and at the same time, the movable block 221 is maintained in an erect state with the rod bar 133 by the elastic member 260, thereby making preparation for next forward movement At this time, the fixed block 222 is inclinedly installed by the elastic member 260 so that the outer circumferential surface of the rod bar 133 is pressed by the upper and lower parts of the internal circumference of the through hole 213 in the lower direction, and thus the rod bar 133 moved by the movable block 221 is fixed not to be moved thanks to the negative pressure.

This prevents the rod bar 133 from being moved using the negative pressure when the movable block 221 makes preparation for a forward motion through the level 240.

By such a method, a rod bar may be gradationally moved in one direction via the movable block being extendably mounted to a cylinder and being linked with a lever which is rotated by the grip of one hand, thereby enabling human tissue to be easily extracted through the syringe 100 to the outside even with the grip of one hand.

Also, by changing the slope of the fixed block 222 that is mounted to the main block 210 and functions to maintain a negative pressure state, a fixation state with the rod bar 133 may be released, whereupon the negative pressure state of the space 121 of the cylinder 120 may be simply released through a simple inclination motion conversion of the fixed block 230 so as to enable the generation of a positive pressure, thereby improving operability of the pressure generating auxiliary device.

As illustrated in FIGS. 8 to 10, another embodiment of the syringe pressure generating device according to the present invention is as follows.

The motion-converting means 220 is synchronized with a rack gear 133*a* formed at one end of the rod bar 133 in a length direction by rotatably installing a pinion gear 260 in the auxiliary device 20 through a central axis 262.

Furthermore, an internal gear 261 having an inclination angle only in one direction is installed inside the pinion gear 260 so that a latch gear 280 elastically synchronized with the internal gear 261 through a spring in the main block 210 fixed to the lever 240 enables the pinion gear 260 to transmit turning force to the internal gear 261 only in one direction through the lever 240.

That is, when the lever 240 is turned by a leverage principle through the grip of the hand, the lever 240 is turned on the basis of the central axis 262 installed at the auxiliary device 200, thereby interlocking with a rotating sphere 270.

At least one groove is formed in an external circumference of the rotating sphere 270, the latch gear 280 is hinge-connected inside the groove, and one end of the latch gear 280 is elastically located upward by the spring 281.

The internal gear 261 and the latch gear 280 are synchronized with each other at an angle of one direction so that the pinion gear 260 can be rotated by the latch gear 280 only in one direction, and the rack gear 133*a* performs a linear motion to the rear by the rotation of the pinion gear 260, thereby interlocking the piston in the inside of the space, and enabling a positive pressure to be generated.

Also, an auxiliary latch gear 290 is hinge-connected to the rear of the auxiliary device, and one end of the auxiliary latch gear is elastically located upward by the spring 281 so that the movement of the rod bar 133 can be controlled by the positive pressure generated at the syringe, thereby preventing the rod bar 133 from being returned to its original position thanks to the positive pressure.

Moreover, as illustrated in FIGS. 11 and 12, the syringe pressure generating device further includes a pressure displaying device.

The pressure displaying device is configured such that the grip goes through the elastic member 150 during transmitting the grip to the piston 131 so that the change amount of a tensioned shape of the elastic member 150 can be changed by the intensity of transmitted pressure, thereby enabling the intensity of pressure to be confirmed to the outside through the measured shape change amount of the elastic member 150.

To realize this, the piston 131 is configured such that a first piston 131*a* and a second piston 131*b* composed in a double structure are coupled to the space while a confirmation member 132 is formed on one side of the first piston 131, and a groove 134 for receiving the confirmation member 132 is formed in the second piston 131*b*.

Furthermore, the first piston 131*a* is moved by the elastic member 150 linked with the second piston 131*b* through the rod bar 133 by connecting the confirmation member 132 of the first piston 131*a* and the groove 134 of the second piston 131*b* using the elastic member 150, thereby enabling positive pressure or negative pressure to be selectively generated in the space.

Thus, based on the gradations 135 of each unit or the change amount in the shape of the elastic member displayed on an external circumference of the confirmation member 132, intensity of the negative or positive pressure may be confirmed according to the change situation of a tensioned and pressed length resulting from self-elasticity of the elastic member 150.

That is, when extracting human tissue such as fat and the like through the syringe, the needle penetrates into a local part of the body, and the rod bar 133 is then moved to the rear, thereby interlocking the first piston 131*a* by pressure of the elastic member 150 connected between the first piston 131*a* and the second piston 131*b*.

When the first piston 131*a* and the second piston 131*b* are moved to the rear of the space 121, a negative pressure is generated in the space located at the front of the first piston 131*a*, thereby enabling human tissue to be extracted through the needle.

Here, when intensity of the self-elasticity of the elastic member 150 is larger than or equal to that of the pressure of the space 121, negative pressure is generated.

In the case of an operator generating a moving speed of the rod bar 133 that is too rapid and the negative pressure generated in the space 121 is overloaded, the result is that when the intensity of the negative pressure is larger than that of the intensity of the self-elasticity of the elastic member 150, the elastic member 150 stretches due to high self-elasticity.

At this time, the operator can confirm the length of the elastic member 150 through the gradations 135 of the confirmation member 132 with the naked eye, thereby confirming that a current pressure generation situation is not normal.

In reverse, in a case of the generation of a positive pressure, when moving the rod bar 133 forwardly after pricking the body with the needle in order to inject fat or medicine filled in the space 121 into the body, the second piston 131*b* enables the first piston 131*a* to be moved forward by pressing the elastic member 150.

When the first piston 131*a* is moved forward, a positive pressure is generated in the space filled with the medicine, thereby enabling the fat and medicine to be injected in the body.

At this time, if the operator increases a forward movement speed of the rod bar 133 by mistake, positive pressure is excessively generated. Thus, when the intensity of the positive pressure becomes higher than a compressive force of the self-elasticity of the elastic member 150, an elastic length of the elastic member 150 becomes shorter.

At this time, the operator may precisely check a pressure change by confirming a shape change amount of the narrowed elastic member 150 or the gradations 135 of the confirmation member 132 with the naked eye.

Here, as illustrated in FIG. 16, the pressure displaying device may be applied to a pressure generating device according to another embodiment, which enables pressure to be generated by operation of the rack gear 133a and the pinion gear 260, and the effect thereof is the same as that of the pressure displaying device.

Also, as illustrated in FIGS. 13 and 14, a pressure displaying device of another embodiment of the pressure generating device is configured as follows.

The pressure displaying device is configured such that the elastic member 150 connected to the rod bar 133 is pressed by the grip during transmitting the grip to the piston 131 so that a change amount of the compressed shape of the elastic member 150 can be changed, thereby enabling intensity of the pressure to be confirmed to the outside through the measured change amount in the shape of the elastic member 150

To realize this, the syringe includes the rod bar 133, a housing 140, a cover 142, and a button 141.

The housing 140 is slidably connected to the external circumference of the rod bar 133.

Furthermore, the cover 142 is fixed to one end of the housing 140, and the button 141 received in the cover 142 is fixed to one end of the rod bar 133.

The elastic member 150 is mounted inside the cover 142, and thus, when the housing 140 is moved by the lever 240, the cover 142 is linked therewith, thereby pressing the elastic member 150.

At this time, when compressive force of the elastic member 150 is higher than or equal to intensity of the pressure being in the space 121 of the cylinder 120, the button 141 is pushed backward by elastic force of the elastic member 150, thereby enabling negative pressure to be generated by moving the piston 131 inside the space 121 using the rod bar 133 integrally fixed to the button 141.

Also, the gradations 135 of each unit are displayed on the rod bar 133 adjacent to a position where the piston 131 is mounted and an external circumference of the button 141 so that situations of the shape change due to the self-elasticity of the elastic member 150 can be confirmed with the naked eye, and a pressure change can be also confirmed using the gradations 135 of each unit, thereby allowing the operator to more easily check a change situation of intensity of the pressure outside the syringe.

Thus, the visualization of pressure can be realized, and at the same time, and intensity of the pressure generated in the space of the syringe can precisely checked, thereby enabling a precise operation for injecting fat or medicine or extracting human tissue to be performed.

Also, as illustrated in FIG. 15, in the syringe, a device for generating pressure using a structure of the rack gear 133a and the pinion gear 260 is configured such that the pressure displaying device mentioned in FIGS. 6a and 6b is installed at one end of the housing 140 having the rack gear 133a formed on the external circumference thereof, so a length change amount in the shape of the elastic member 150 and a numerical change amount of the gradations of each unit can be checked in the same way as described in the section relating to FIGS. 6a and 6b, thereby ensuring easy and exact visualization of pressure changes.

Here, the elastic member 150 is composed of rubber or a spring. If a material or structure has self-elasticity, any material can be also applied to the elastic member 150.

The invention claimed is:

1. A syringe pressure generating and pressure displaying device, which is applied to a syringe, comprising:
   a tip portion to which a needle is connected;
   a cylinder connected to the tip portion to form a space therein, and having a cylinder flange formed in an opening end of the space;
   a pressure means configured to inject medicine or extract human tissue through the needle using a negative pressure or a positive pressure by changing pressure of the space with a piston being linked with a pushing or pulling motion of a rod bar connected to the piston in the space,
   wherein an auxiliary device is detachably attached to the cylinder flange to use all of the cylinder while the rod bar is installed in the auxiliary device so as to pass there through, and a first grip on a lever that is hinge-connected to the auxiliary device so as to be disposed horizontally in line with the syringe creates a rotational motion acting due to a leverage principle, whereupon the rotational motion is converted into a linear motion via a motion-converting means, and the rod bar and the piston are moved with increased force;
   wherein the auxiliary device is configured such that a main block fixed to the cylinder flange so as to be disposed horizontally in line with the cylinder is provided, and a movable block and a fixed block each provided with a through hole for enabling the rod bar to pass through by forming a movable space and a fixed space each having an open lower part are disposed in the main block, wherein the negative pressure is generated in such a manner that the movable block and the fixed block are in close contact with the movable space and the fixed space in one direction by an elastic member, and thus by rotation of the lever that is hinge connected to a front of the main block, a lower part of the movable block is pushed by a pressing projection formed at an end of the lever so as to cause an inclination change and so as to be moved backward, whereupon an outer circumferential surface of the rod bar is pressed by upper and lower corners of an internal circumference of the through hole in a lower direction, thereby enabling the rod bar to be moved to a rear of the cylinder, and at the same time, the lever is recovered in an original state of the lever through a spring mounted to a hinge-connected part when the grip is released, and the movable block is maintained in an erect situation with the rod bar by the elastic member so as to arrange forward movement in next order;
   wherein a guide block through which the rod bar passes is connected to an inlet of the space of the cylinder so as to support movement of the rod bar;
   wherein the guide block is located within an inner circumferential surface of the cylinder and the outer surface of the rod bar so that the guide is kept blocked from the outside even when the rod bar is moved,
   wherein the cylinder flange is connected to the guide block is located at an entrance of the cylinder space , and when the rod bar is moved by the lever, the guide block, the rod bar and the cylinder flange together isolate the cylinder space from the outside space, and
   wherein a fixing clip having a fixing jaw formed at a front thereof is located in the main block so that the cylinder flange can be detachably inserted into the fixing jaw by rotation of the cylinder flange.

2. The device of claim 1, wherein the fixed block is installed in the fixed space so that the lower part of the fixed block can be partially exposed, and so as to pass through the rod bar, and is installed to be inclined by the elastic member so that the outer circumferential surface of the rod bar can be pressed by the upper and the lower corners of the internal circumference of the through hole in the lower direction, thereby enabling the rod bar moved by the movable block to be immovably fixed due to the negative pressure, wherein when a fixing situation of the rod bar is released, by pulling out the lower part of the fixed block and converting the fixed block into the erect situation with the rod bar, the through hole of the rod bar enables the outer circumferential surface of the rod bar to be released from a pressure situation.

3. The device of claim 1, wherein a second grip goes through the elastic member during transmitting the second grip to the piston so that a change amount in a tensioned shape of the elastic member can be changed by an intensity of transmitted pressure, thereby enabling an operator to confirm the intensity of pressure to an outside through measurement of the change amount in the shape of the elastic member.

4. The device of claim 1, wherein the elastic member connected to the rod bar is pressed during transmitting a second grip to the piston so that a change amount in a pressed shape of the elastic member can be changed by an intensity of transmitted pressure, thereby enabling an operator to confirm the intensity of pressure to an outside through measurement of the change amount in the shape of the elastic member.

5. The device of claim 4, wherein the rod bar, and a housing slidably connected on the outer circumference of the rod bar are provided such that a cover is fixed to one end of the housing, and a button is fixed to one end of the rod bar so that the button is partially received inside the cover, wherein the negative pressure is generated in such a manner that when the elastic member is fixed inside the cover, and the housing is moved by the lever, the elastic member is pressed, and thus when compressive force of the elastic member is equal to or higher than pressure of the space of the cylinder, the button is indirectly moved backward, thereby interlocking the rod bar, wherein gradations of each unit are displayed on the button and the outer circumference of the rod bar so as to enable an operator to confirm a changed shape length of the elastic member due to the self-elasticity of the elastic member and thus to check intensity of the negative pressure or the positive pressure.

6. The device of claim 1, wherein the piston is configured such that a first piston and a second piston formed in a double structure are connected to the space of the cylinder, and a confirmation member is formed at one side of the first piston, a groove for receiving the confirmation member is formed in the second piston so that the negative or positive pressure can be selectively generated in the space of the cylinder by connecting the confirmation member of the first piston and the groove of the second piston using the elastic member and moving the first piston using the elastic member being linked with the second piston via the rod bar, wherein a size of the negative or positive pressure generated in the space can be confirmed based on a changed shape length of the elastic member due to the elasticity of the elastic member through gradations of each unit displayed on an external circumference of the confirmation member.

* * * * *